(12) United States Patent
Di Marzo et al.

(10) Patent No.: US 7,902,251 B2
(45) Date of Patent: *Mar. 8, 2011

(54) METHOD FOR TREATING PAIN

(75) Inventors: Vincenzo Di Marzo, Pozzuoli (IT);
Luciano De Petrocellis, Pozzuoli (IT);
Sabatino Malone, Brusciano-Naples (IT); Vito De Novellis, S. Maria Capua Vetere (IT)

(73) Assignee: Allergan, Inc., Irvine, CA (US)

( * ) Notice: Subject to any disclaimer, the term of this patent is extended or adjusted under 35 U.S.C. 154(b) by 923 days.

This patent is subject to a terminal disclaimer.

(21) Appl. No.: 11/549,262

(22) Filed: Oct. 13, 2006

(65) Prior Publication Data
US 2007/0088072 A1  Apr. 19, 2007

Related U.S. Application Data

(60) Provisional application No. 60/728,940, filed on Oct. 19, 2005.

(51) Int. Cl.
*A01N 43/38* (2006.01)
*A61K 31/40* (2006.01)
*C07D 209/18* (2006.01)

(52) U.S. Cl. ........................... 514/419; 548/495

(58) Field of Classification Search ............... 514/419; 548/495
See application file for complete search history.

(56) References Cited

U.S. PATENT DOCUMENTS

| 4,658,038 A | 4/1987 | Tamir et al. | |
|---|---|---|---|
| 6,306,890 B1 * | 10/2001 | Kalgutkar et al. | 514/419 |
| 2004/0122089 A1 | 6/2004 | Martin et al. | |

FOREIGN PATENT DOCUMENTS

| WO | WO 99/23070 | 5/1999 |
|---|---|---|
| WO | WO03/008632 | 1/2003 |
| WO | WO2005/001041 | 1/2005 |

OTHER PUBLICATIONS

Fowler et al. (Biochem Pharmacology, 62, 2001, 517-526).*
Huang et al. (Cannabinoids as Therapeutics, Ed. Mecholulam, 2005, p. 149-163).*

Schindler, "128. Uber einige in 2-Stellung substituierte 5-Hydroxyindole", Helvetica Chimica Acta, 1130-1136, 1957.
Jacobsson et al, "Inhibition of Rat C6 Glioma Cell Proliferation by Endogenous and Synthetic Cannabinoids. Relative Involvement of Cannabinoid and Vanilloid Receptors", Journal of Pharmacology and Experimental Therapeutics, vol. 299, No. 3, Dec. 2001, pp. 951-959.
Bifulco et al, "A new strategy to block tumor growth by inhibiting endocannabinoid inactivation", FASEB Journal, vol. 18, 2004, pp. 1606-1608.
Bisogno et al, "Arachidonoylserotonin and other novel inhibitors of fatty acid amide hydrolase", Biochemical and Biophysical Research Communications, 1998, pp. 515-522.
Szallasi et al, "Vanilloid receptor TRPV1 antagonists as the next generation of painkillers. Are we putting the cart before the horse?" Journal of Medicinal Chemistry, vol. 47, No. 11, pp. 2717-2723, 2004.
Suplita et al, "Inhibition of fatty-acid amide hydrolase enhances cannabinoid stress-induced analgesia: Sites of action in the dorsolateral periaqueductal gray and rostral ventromedial medulla" Neuropharmacology, Dec. 2005, pp. 1201-1209.
Lynch et al, "Attenuation of mechanical allodynia by clinically utilized drugs in a rat chemotherapy-induced neuropathic pain model", Pain, vol. 110, Jul. 2004-pp. 56-63.
Rodella et al, "AM404, an inhibitor of anadamide reuptake decreases Fox-immunoreactivity in the spinal cord of neuropathic rats after non-oxious stimulation", European Journal of Pharmacology, vol. 508, Jan. 31, 2005, pp. 139-146.
Capasso et al, "Hydrolase Controls Mouse Intestinal Motility in Vivo", Gastroenterology, vol. 129, Sep. 2005, pp. 941-951.

* cited by examiner

*Primary Examiner* — Sreeni Padmanabhan
*Assistant Examiner* — Umamaheswari Ramachandran
(74) *Attorney, Agent, or Firm* — Joel B. German; Debra D. Condino; Allergan, Inc.

(57) ABSTRACT

The present invention provides pharmaceutical compositions useful in a method for treating neuropathic pain, said method comprising administration of a pain-ameliorating effective amount of the compound according to formula I

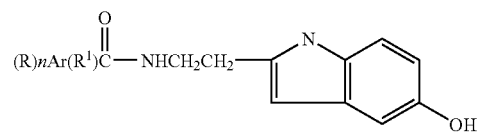

wherein R is an alk(en)yl group, R1 is an alkylen(yl) group, n is 0 or 1 and Ar is a carbocyclic aryl group.

3 Claims, No Drawings

METHOD FOR TREATING PAIN

CROSS REFERENCE TO RELATED APPLICATIONS

This application is based on, and claims the benefit of, U.S. Provisional Application No. 60/728,940, filed Oct. 19, 2005, and which is incorporated herein by reference.

BACKGROUND OF THE INVENTION

1. Field of the Invention

The present invention relates to the treatment or prevention of pain or nociception.

2. Related Art

Pain is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult, however, many individuals suffer with severe and continuous pain.

Pain that is caused by damage to neural structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain.

The level of stimulation at which pain becomes noted is referred to as the "pain threshold." Analgesics are pharmaceutical agents which relieve pain by raising the pain threshold without a loss of consciousness. After administration of an analgesic drug a stimulus of greater intensity or longer duration is required before pain is experienced. In an individual suffering from hyperalgesia an analgesic drug may have an anti-hyperalgesic effect. In contrast to analgesics, agents such as local anaesthetics block transmission in peripheral nerve fibers thereby blocking awareness of pain. General anaesthetics, on the other hand, reduce the awareness of pain by producing a loss of consciousness.

BRIEF SUMMARY OF THE INVENTION

It has now been discovered that certain compounds which exhibit the properties of blocking transient receptor potential vanilloid type 1 (TRPV1) channels and activating cannabinoid $CB_1$ receptors have a utility for the amelioration of pain and particularly for the amelioration of neuropathic pain. The compounds of this invention are analogues and/or homologues of the compound N-arachidonyl serotonin (AA-5-HT).

Therefore, in one aspect, the method of the present invention utilizes a N-alk(en)yl carbocyclic aryl alk(yl)enyl carboserotonin adduct to treat pain. The compounds utilized in the method of the present invention are amides of hydrocarbyl acids and serotonin wherein said hydrocarbyl moiety includes enchained aryl radicals. That is, the compounds are N-(alkyl)$_n$ carbocyclic aryl alkanoyl-serotonin compounds wherein n is 0 or 1 and said (alkyl)$_n$ carbocyclic aryl alkanoyl radical includes from 7 to 30 carbon atoms, e.g. from 8 to 22 carbon atoms. Said alkyl group and said alkanoyl group may include 1 or more, e.g. 1-3 unsaturated bonds. That is, said alkyl group may be an alkenyl group, including a conjugated alkenyl group. Thus, the designation as alk(en)yl is utilized. Said alkanoyl group may be an alkenoyl group. Thus, the designation alk(yl)enyl carbo is utilized. Said compound may be represented by the formula I

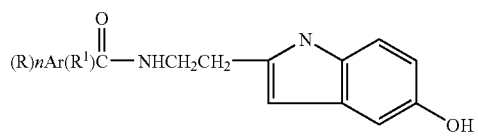

wherein R is an alk(en)yl group, $R^1$ is an alkylen(yl) group, n is 0 or 1 and Ar is a carbocyclic aryl group.

Preferably R is an alkyl or alkenyl group comprising from 1 to 7 carbon atoms and more preferably R is an methyl alkylene or methyl alkenyl group such as $CH_3CH_2$, $CH_3CH_2CH_2$, $CH_3CH_2CH_2CH_2$, $CH_3CHCH$, or $CH_3CHCHCH_2CHCHCH_2$.

Preferably $R^1$ is an alkylene group consisting from 3 to 6 carbon atoms, such as $CH_2CH_2CH_2$, $CH_2CH_2CH_2CH_2$, $CH_2CH_2CH_2CH_2CH_2CH_2$, etc.

Preferably Ar is selected from the group consisting of phenyl, naphthyl and biphenyl and lower alkyl substituted derivatives thereof, i.e. $C_1$ to $C_4$ alkyl substituted derivatives thereof.

For example, the compounds of formula I may be selected from the group consisting of

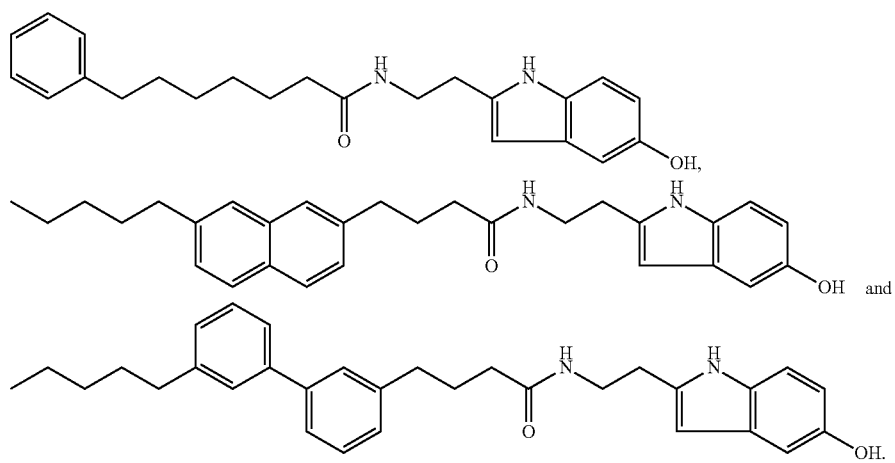

The compounds of this invention may be prepared by reacting serotonin or an analogue or homologue thereof with a carboxylic acid to form the corresponding amide of said carboxylic acid and serotonin (or analogue or homologue thereof). This reaction may be carried out at conditions known in the art for preparing amides of fatty acids e.g., which fatty acids have similar reaction properties as the above carboxylic acids.

In another aspect, the invention provides a method for the treatment of pain using a compound in accord with formula I, the method comprising administering a pain-ameliorating effective amount of the compound.

In another embodiment, the method comprises administration of a pain-ameliorating effective amount of a compound according to formula I in the form of a pharmaceutical composition comprising a compound according to formula I as an active ingredient together with one or more pharmaceutically-acceptable additives.

In a further embodiment, the method comprises binding a compound according to formula I to the fatty amide hydrolase of a warm-blooded animal, such as a human being, so as to beneficially enhance endocannabinoid levels and increase the activity of CB1 receptors.

In a further embodiment, the method comprises binding a compound according to formula I to the fatty acid amide hydrolase of a warm-blooded animal, such as a human being, so as to enhance endocannabinoid levels and activate cannabinoid receptors in said animals to thereby ameliorate pain.

Yet other aspects of the invention are pharmaceutical compositions which contain the compound in accord with formula I and the use of the compound in accord with formula I for the preparation of medicaments and pharmaceutical compositions.

DETAILED DESCRIPTION OF THE INVENTION

Genetic or pharmacological targeting of fatty acid amide hydrolase (FAAH), one of the enzymes catalysing endocannabinoid degradation, was shown to result in analgesic and anti-hyperalgesic actions that are due to the "indirect" activation (via enhancement of endocannabinoid levels) of cannabinoid $CB_1$ receptors. Additionally, genetic or pharmacological targeting of transient receptor potential vanilloid type 1 (TRPV1) channels was found to abolish thermal and inflammatory analgesia. We describe a class of "hybrid" FAAH inhibitors/TRPV1 antagonists with high efficacy against inflammatory hyperalgesia. These "hybrid" FAAH inhibitors are homologues and/or analogues of AA-5-HT and have the general formula I:

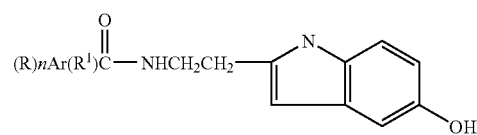

wherein R is an alk(en)yl group $R^1$ is an alkylen(yl) group, n is 0 or 1 and Ar is a carbocyclic aryl group.

Preferably R is an alkyl or alkenyl group comprising from 1 to 7 carbon atoms and more preferably R is an methyl alkylene or methyl alkenyl group such as $CH_3CH_2$, $CH_3CH_2CH_2$, $CH_3CH_2CH_2CH_2$, $CH_3CHCH$, or $CH_3CHCHCH_2CHCHCH_2$.

Preferably $R^1$ is an alkylene group consisting from 3 to 6 carbon atoms, such as $CH_2CH_2CH_2$, $CH_2CH_2CH_2CH_2$, $CH_2CH_2CH_2CH_2CH_2CH_2$, etc.

Preferably Ar is selected from the group consisting of phenyl, naphthyl and biphenyl and lower alkyl substituted derivatives thereof, i.e. $C_1$ to $C_4$ alkyl substituted derivatives thereof.

For example, the compounds of formula I may be selected from the group consisting of

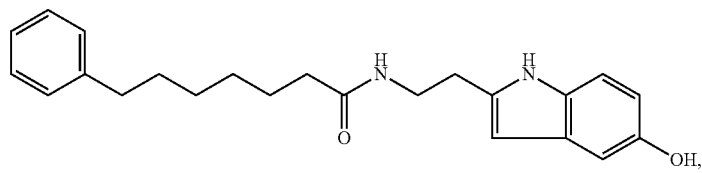

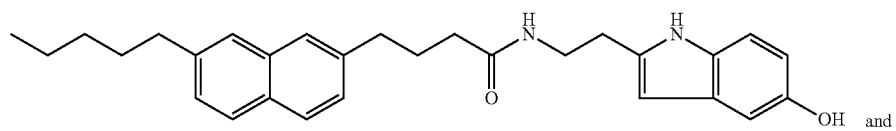

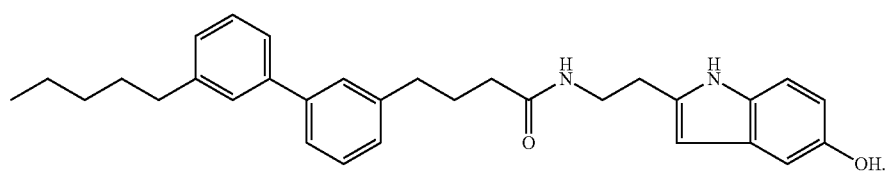

These compounds inhibit FAAH and, also interact, by blocking their activation by capsaicin, with TRPV1 channels, whose gating plays a permissive role in the development of hyperlagesia.

When injected directly into the periaqueductal grey (PAG) of rats, the compounds of this invention potently inhibit both phases of the nociceptive response to formalin injected into the rat paw and concomitantly elevate anandamide levels in this area of the brainstem. The effect is counteracted by the $CB_1$ receptor antagonist AM251 (nmol/rat) and is occluded by the TRPV1 antagonist, capsazepine (6 nmol/rat). Thus, while not wishing to be bound by theory, it is believed that the compounds of formula I ameliorate pain by the dual mechanism of action of both "indirect" activation of $CB_1$ and antagonism of TRPV1. The compound acts at the supraspinal level by blocking the inhibitory effect of formalin on the OFF cells of the rostral ventromedial medulla, which receive synapses with cells from the PAG. Also this effect is reversed by AM251 and occluded by capsazepine. When injected into the paw, these compounds, selectively block the $2^{nd}$, inflammatory phase of the nocifensive response to formalin, again in a way counteracted by AM251 and occluded by capsazepine, thus suggesting also a peripheral mode of action.

The compounds are novel agents against anti-inflammatory pain, acting by enhancing endocannabinoid levels (via FAAH inhibition) and at the same time by antagonizing TRPV1.

The advantage of having in one molecule a FAAH inhibitor and a TRPV1 antagonist comes from the several experimental observations suggesting that FAAH inhibitors (i.e. "indirect" agonists of cannabinoid and fatty acid amide receptors) as well as direct cannabinoid receptor agonists (both CB1 and CB2) are very promising against inflammatory and neuropathic pain, and so are compounds that block TRPV1 receptors. However, different populations of neurons/cells and different mechanisms are involved in CB1/CB2- and TRPV1-mediated anti-inflammatory and anti-hyperalgesic/anti-allodynic effects. Therefore, if for example following nerve injury, only one of these different populations is destroyed, a compound only acting on that population will be ineffective, whereas a compound with "hybrid" activity will always be more effective. On the other hand if different nociceptive mechanisms cause pain, a drug targeting more of these mechanisms will be more efficacious than a drug specific for only one of them.

To use the compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition.

Suitable pharmaceutical compositions that contain the compounds of the invention may be administered in conventional ways, for example by oral, topical, parenteral, buccal, nasal, vaginal or rectal administration or by inhalation. For these purposes a compound of the invention may be formulated by means known in the art into the form of for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention a pharmaceutical composition of this invention may also contain one or more other pharmacologically-active agents, or such pharmaceutical composition may be simultaneously or sequentially co-administered with one or more other pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weights age and sex of the patient being treated and on the particular disease condition being treated according to principles known in the art. A preferred dosage regime is once daily.

A further embodiment of the invention provides a pharmaceutical composition which contains a compound of the invention as defined herein or a pharmaceutically-acceptable salt thereof, in association with a pharmaceutically-acceptable additive such as an excipient or carrier.

A yet further embodiment of the invention provide the use of the compound of the invention, or a pharmaceutically-acceptable salt thereof, in the manufacture of a medicament useful for indirectly blocking the TRPV1 channel in a warm-blooded animal such as a human being.

Still another embodiment of the invention provides a method of binding the compound of the invention to the FAAH channel of a warm-blooded animal, such as a human being, in need of treatment for pain, which method comprises administering to said animal an effective amount of a compound of formula I or a pharmaceutically-acceptable salt thereof.

A yet further embodiment of the invention comprises the use of the compound of the invention, or a pharmaceutically-acceptable salt thereof, in the manufacture of a medicament useful for activating the cannabinoid $CB_1$ receptor in a warm-blooded animal such as a human being.

Still another embodiment of the invention provides a method of binding the compound of the invention to the fatty acid amide hydrolase of a warm-blooded animal, such as a human being, in need of treatment for pain, which method comprises administering to said animal an effective amount of a compound of formula I or a pharmaceutically-acceptable salt thereof.

The foregoing description details specific methods and compositions that can be employed to practice the present invention, and represents the best mode contemplated. Thus, however detailed the foregoing may appear in text, it should not be construed as limiting the overall scope hereof, rather, the ambit of the present invention is to be governed only by the lawful construction of the appended claims.

What is claimed is:

1. A method for treating neuropathic pain, said method comprising administration of a pain-ameliorating effective amount of N-alk(en)yl carbocyclic aryl alk(yl)enyl-carbo-serotonin adduct represented by formula I

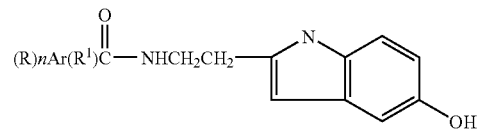

wherein R is an alk(en)yl group, $R^1$ is an alkylen(yl) group, n is 0 or 1 and Ar is a carbocyclic aryl group.

2. The method of claim 1 wherein the compound of formula I may be selected from the group consisting of

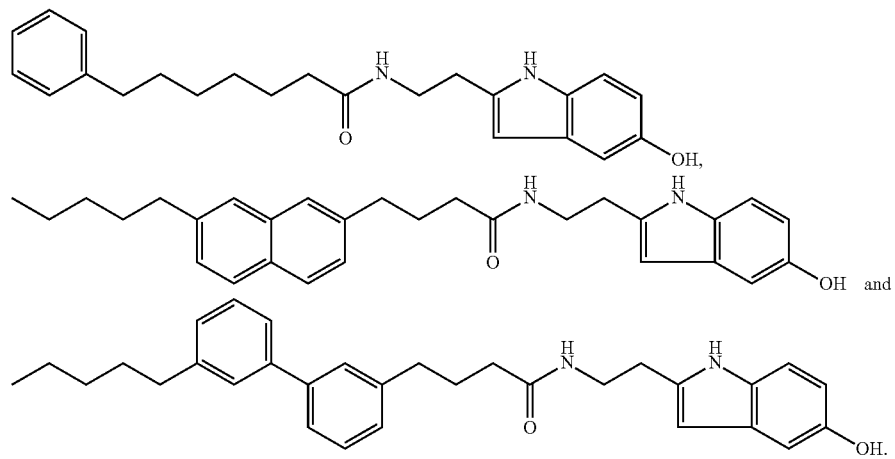

3. A method of treating neuropathic pain, said method comprising administration of a pain-ameliorating amount of a composition comprising the N-alk(en)yl carbocyclic aryl alk(yl)enyl-carbo-serotonin adduct of claim 1 to a warm-blooded animal to thereby bind the N-alk(en)yl carbocyclic aryl alk(yl)enyl-carbo-serotonin adduct to the TRPV1 channel so as to beneficially inhibit the activity of said channel and activate the cannabinoid receptor to enhance endocannabinoid levels in said animal to thereby ameliorate pain.

* * * * *

UNITED STATES PATENT AND TRADEMARK OFFICE
CERTIFICATE OF CORRECTION

| | | |
|---|---|---|
| PATENT NO. | : 7,902,251 B2 | Page 1 of 1 |
| APPLICATION NO. | : 11/549262 | |
| DATED | : March 8, 2011 | |
| INVENTOR(S) | : Di Marzo et al. | |

It is certified that error appears in the above-identified patent and that said Letters Patent is hereby corrected as shown below:

On Title page, Item (56), under "OTHER PUBLICATIONS", in column 1, line 2, delete "Mecholulam," and insert -- Mechoulam, --, therefor.

On Title page, Item (56), under "OTHER PUBLICATIONS", in column 2, line 24, delete "anadamide" and insert -- anandamide --, therefor.

On Title page, Item (56), under "OTHER PUBLICATIONS", in column 2, line 26, delete "non-oxious" and insert -- non-noxious --, therefor.

On Title page, Item (57), under "ABSTRACT", in column 2, line 6, delete "R1" and insert -- $R^1$ --, therefor.

In column 3, line 22, delete "CB1" and insert -- $CB_1$ --, therefor.

In column 4, line 21, delete "group" and insert -- group, --, therefor.

In column 5, line 4, delete "hyperlagesia." and insert -- hyperalgesia. --, therefor.

In column 5, line 10, delete "antagonist" and insert -- antagonist, --, therefor.

In column 5, line 57, delete "of" and insert -- of, --, therefor.

In column 6, line 9, delete "weights" and insert -- weight, --, therefor.

In column 6, line 47, delete "hereof," and insert -- hereof; --, therefor.

In column 6, line 64, delete "group ," and insert -- group, --, therefor.

Signed and Sealed this
Third Day of May, 2011

David J. Kappos
*Director of the United States Patent and Trademark Office*